US011180475B2

(12) United States Patent
Wu et al.

(10) Patent No.: US 11,180,475 B2
(45) Date of Patent: Nov. 23, 2021

(54) CRYSTAL FORM I OF A 5-AMINOPYRAZOLE CARBOXAMIDE COMPOUND AS BTK INHIBITOR

(71) Applicant: SinoMab BioScience Limited, New Territories (HK)

(72) Inventors: Yuchuan Wu, Beijing (CN); Xi Chen, Beijing (CN); Shaoqiang Huang, Beijing (CN); Yonghan Hu, Beijing (CN)

(73) Assignee: SinoMab BioScience Limited, New Territories (HK)

( * ) Notice: Subject to any disclaimer, the term of this patent is extended or adjusted under 35 U.S.C. 154(b) by 0 days.

(21) Appl. No.: 16/762,830

(22) PCT Filed: Nov. 8, 2018

(86) PCT No.: PCT/CN2018/114666
§ 371 (c)(1),
(2) Date: May 8, 2020

(87) PCT Pub. No.: WO2019/091440
PCT Pub. Date: May 16, 2019

(65) Prior Publication Data
US 2020/0361902 A1 Nov. 19, 2020

(30) Foreign Application Priority Data
Nov. 10, 2017 (CN) .......................... 201711104892.X

(51) Int. Cl.
*C07D 401/14* (2006.01)
*A61K 31/444* (2006.01)

(52) U.S. Cl.
CPC .......... *C07D 401/14* (2013.01); *A61K 31/444* (2013.01); *C07B 2200/13* (2013.01)

(58) Field of Classification Search
CPC .............. C07D 401/14; C07B 2200/13; A61K 31/444; A61P 7/02; A61P 35/00; A61P 37/02; A61P 43/00
(Continued)

(56) References Cited

U.S. PATENT DOCUMENTS 9,926,299 B2    3/2018   Han et al.
10,112,922 B2   10/2018  Han et al.
(Continued)

FOREIGN PATENT DOCUMENTS

CN    103848810 A    6/2014
CN    105008344 A    10/2015
(Continued)

OTHER PUBLICATIONS

International Search Report and Written Opinion for Application No. PCT/CN2018/114666, dated Feb. 13, 2019, 10 pages.
(Continued)

*Primary Examiner* — Taylor V Oh
(74) *Attorney, Agent, or Firm* — McCarter & English, LLP; Steven G. Davis; Wei Song

(57) ABSTRACT

Disclosed is a new crystal form of a 5-aminopyrazole carboxamide compound as shown in Formula (I). Also disclosed are a preparation method for said crystal form of said compound, a pharmaceutical composition of said crystal form of said compound, and uses thereof.
(Continued)

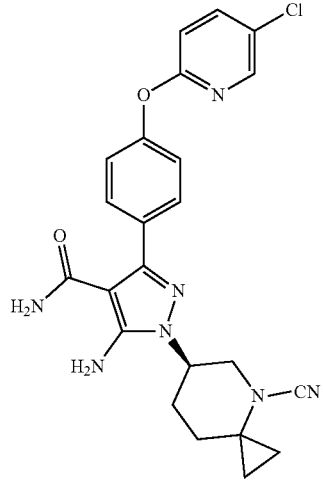

(I)

7 Claims, 2 Drawing Sheets

(58) Field of Classification Search
USPC .................................................... 514/318
See application file for complete search history.

(56) References Cited

U.S. PATENT DOCUMENTS

| 10,266,513 B2 | 4/2019 | Springer et al. |
| 2019/0152952 A1 | 5/2019 | Wu |

FOREIGN PATENT DOCUMENTS

| CN | 105085474 A | 11/2015 |
| CN | 107382973 A | 11/2017 |
| CN | 107383013 A | 11/2017 |
| WO | 2014/068527 A1 | 5/2014 |
| WO | 2017/198050 A1 | 11/2017 |
| WO | 2019/091441 A1 | 5/2019 |

OTHER PUBLICATIONS

International Search Report and Written Opinion for Application No. PCT/CN2018/114669, dated Jan. 8, 2019, 12 pages.

CRYSTAL FORM I OF A 5-AMINOPYRAZOLE CARBOXAMIDE COMPOUND AS BTK INHIBITOR

CROSS-REFERENCE TO RELATED APPLICATIONS

This application is a U.S. national stage filing, under 35 U.S.C. § 371(c), of International Application No. PCT/CN2018/114666, filed on Nov. 8, 2018, which claims priority to Chinese Patent Application No. 201711104892.X, filed on Nov. 10, 2017. The entire contents of each of the aforementioned applications are incorporated herein by reference.

TECHNICAL FIELD

The present invention belongs to the field of medicinal chemistry, and in particular, relates to a novel 5-aminopyrazole carboxamide compound with high efficiency, good selectivity and excellent pharmacokinetic properties as a BTK inhibitor, a crystalline form thereof, a method for preparing the compound and a crystalline form thereof, and a pharmaceutical composition comprising the compound or a crystalline form thereof.

BACKGROUND OF THE INVENTION

Protein kinases are the largest family of biological enzymes in human, including more than 500 proteins. In particular, for tyrosine kinases, the phenolic functional group on the tyrosine residue can be phosphorylated, thereby playing an important role in biological signaling. The tyrosine kinase family has members that control cell growth, migration and differentiation. Abnormal kinase activities have been shown to be closely associated with a variety of human diseases, including cancers, autoimmune diseases, and inflammatory diseases.

Bruton tyrosine kinase (BTK) is a cytoplasmic non-receptor tyrosine kinase, belonging to the TEC kinase family (comprising a total of 5 members: BTK, TEC, ITK, TXK, and BMX). The BTK gene is located on Xq21.33-Xq22 of the chromosome X, with a total of 19 exons, spanning 37.5 kb of the genomic DNA.

BTK is expressed on almost all hematopoietic cells except T cells and plasma cells, and especially plays an essential role in development, differentiation, signaling and survival of B lymphocytes. B cells are activated via B cell receptors (BCR), and BTK plays a critical role in the BCR signaling pathway. The activation of BCR on B cells will cause activation of BTK, leading to an increase in the concentration of downstream phospholipase C (PLC), and activation of the IP3 and DAG signaling pathways. The signaling pathway can promote cell proliferation, adhesion and survival. A mutation in BTK gene can cause X-Linked agammaglobulinemia (XLA), a rare hereditary B-cell specific immunodeficiency disease. In this disease, the function of BTK is inhibited, leading to suppression of the production or maturation of B cells. Male patients with XLA have almost no B cells, and a few of circulating antibodies, and are prone to serious or even fatal infections. The above facts strongly prove that BTK plays an extremely important role in the growth and differentiation of B cells.

Small molecule BTK inhibitors can bind to BTK, inhibit autophosphorylation of BTK, and prevent activation of BTK. This can block the signaling of the BCR pathway, inhibit proliferation of B lymphoma cells, and destroy adhesion of tumor cells, thereby promoting apoptosis of the tumor cells. That is, it can induce apoptosis. This makes BTK an attractive drug target in B-cell-related cancers, especially B-cell lymphoma and leukemia, such as non-Hodgkin's lymphoma (NHL), chronic lymphocytic leukemia (CLL), relapsed or refractory mantle cell lymphoma (MCL), etc.

In addition to the inhibitory effects on B-cell lymphoma and leukemia, BTK inhibitors can also inhibit production of B-cell autoantibodies and cytokines. In autoimmune diseases, B cells present self-antigens, and promote activation of T cells to secret pro-inflammatory factors, which not only cause tissue damages, but also activate B cells to produce a large amount of antibodies, triggering autoimmune responses. T and B cells interact to form a feedback regulatory chain, which leads to an uncontrolled autoimmune response and exacerbates histopathological damages. Therefore, BTK can act as a drug target for autoimmune diseases, such as rheumatoid arthritis, systemic lupus erythematosus (SLE), and allergic diseases (e.g., esophagitis, and the like).

In addition, there are reports that BTK inhibitors can be used in combination with chemotherapeutic agents or immune checkpoint inhibitors, and exhibit good therapeutic effects on a variety of solid tumors in clinical trials.

Among the currently commercially available drugs, Ibrutinib is an irreversible BTK inhibitor jointly developed by Pharmacyclics and Johnson & Johnson. It was approved by the FDA for the treatment of mantle cell lymphoma (MCL) and chronic lymphocytic leukemia (CLL) in November 2013 and February 2014, respectively. Ibrutinib was designated as a new "breakthrough" drug by the FDA. It exerts its therapeutic effect by inactivating the BTK enzyme through reacting with the sulfhydryl group of the cysteine in BTK to form a covalent bond. However, Ibrutinib can be easily metabolized during administration (it is oxidized by a metabolic enzyme into a dihydroxylated product or inactivated by challenge of other mercapto-containing enzymes, cysteine, glutathione, and the like), thereby compromising the efficacy. The clinical dosage of Ibrutinib can be up to 560 mg per day, which increases the burden on patients. Moreover, Ibrutinib has a certain inhibitory effect on some kinases other than BTK. In particular, the inhibition on EGFR can lead to more serious adverse reactions such as rash and diarrhea. Therefore, there is still a need for development of a new BTK inhibitor that is more efficient, selective, and has good pharmacokinetic properties for the treatment of related diseases.

SUMMARY OF THE INVENTION

The present inventors have developed a novel 5-aminopyrazole carboxamide compound, which is an effective, safe, and highly selective inhibitor of the protein kinase BTK. It is a new covalent bond inhibitor. It improves the affinity to its target by changing the rate of reaction with cysteine, thereby improving its efficacy, selectivity and safety. It has a structure as shown in Formula (I):

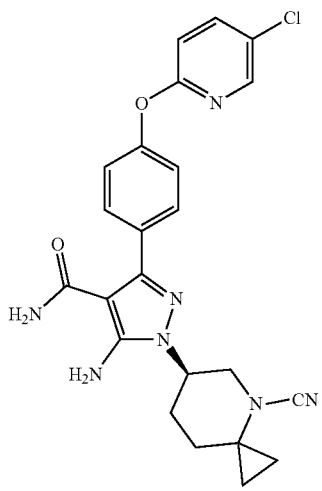

(I)

It has a chemical name of (R)-5-amino-3-(4-((5-chloropyridin-2-yl)oxy)phenyl)-1-(4-cyano-4-azaspiro[2.5]oct-6-yl)-1H-pyrazole-4-carboxamide (abbreviated as API).

The first object of the present invention is to provide a crystalline form I of the compound as shown in Formula (I) as above.

The second object of the present invention is to provide a method for preparing the crystalline form I of the compound as shown in Formula (I) as above.

The third object of the present invention is to provide a pharmaceutical composition comprising the crystalline form I of the compound as shown in Formula (I) as above.

The fourth object of the present invention is to provide use of the crystalline form I of the compound as shown in Formula (I) as above.

In one embodiment, the present invention provides a crystalline form I of the 5-aminopyrazole carboxamide compound as shown in Formula (I), which has an X-ray powder diffraction pattern with characteristic peaks (expressed by 2θ angle) (±0.2°) at 5.8, 9.3, 10.9, 16.4, 18.4, 20.3, 20.9, 21.8, 22.4, 23.0, 24.4, 27.1, 30.0, 31.2, and 31.9, as measured under Cu-K radiation at a wavelength of 1.54179 Å.

In one embodiment, the present invention provides a crystalline form I of the 5-aminopyrazole carboxamide compound as shown in Formula (I), which has an X-ray powder diffraction pattern substantially as shown in FIG. 1.

In one embodiment, the present invention provides a method for preparing the crystalline form I of the 5-aminopyrazole carboxamide compound as shown in Formula (I), comprising the steps of: dissolving the 5-aminopyrazole carboxamide compound as shown in Formula (I) in a good solvent; then adding a poor solvent to the resulting solution while stirring to give a suspension; centrifuging the suspension after continued stirring; and drying the resulting solid under vacuum to afford a crystalline form I of the 5-aminopyrazole carboxamide compound as shown in Formula (I).

Preferably, the good solvent is selected from tetrahydrofuran, and the poor solvent is selected from the group consisting of water, n-heptane, and the like.

Preferably, the ratio of the good solvent to the poor solvent is in the range of 1:2 (v/v) to 1:4 (v/v); more preferably, when the good solvent is tetrahydrofuran and the poor solvent is water, the ratio is 1:2 (v/v); and when the good solvent is tetrahydrofuran and the poor solvent is n-heptane, the ratio is 1:4 (v/v).

Preferably, the vacuum drying is performed at a temperature ranging from room temperature to 100° C., more preferably 25 to 80° C., more preferably 25 to 50° C., and most preferably at 30° C.

In one embodiment, the present invention provides a pharmaceutical composition comprising an effective amount of the 5-aminopyrazole carboxamide compound as shown in Formula (I) or crystalline form I thereof according to the present invention, and a pharmaceutically acceptable carrier.

The pharmaceutical composition of the present invention can be formulated as a solid, semi-solid, liquid or gaseous formulation, such as a tablet, capsule, powder, granule, ointment, solution, suppository, injection, inhalant, gel, microsphere, or aerosol.

The pharmaceutical composition of the present invention can be prepared by a method well-known in the pharmaceutical field. For example, the actual method for preparing the pharmaceutical composition is known to those skilled in the art. See, for example, The Science and Practice of Pharmacy, 20th Edition (Philadelphia College of Pharmacy and Science, 2000).

The administration route of the pharmaceutical composition of the present invention includes, but is not limited to, oral, topical, transdermal, intramuscular, intravenous, inhalation, parenteral, sublingual, rectal, vaginal and intranasal administration. For example, the dosage forms suitable for oral administration include capsules, tablets, granules, syrups, etc. The compound of Formula (I) of the present invention contained in these formulations can be in the form of a solid powder or granule; a solution or suspension in an aqueous or non-aqueous liquid; a water-in-oil or oil-in-water emulsion; and the like. The above dosage forms can be prepared from the active compound and one or more carriers or vehicles by a conventional pharmaceutical method. The above carrier needs to be compatible with the active compound or other excipients. For solid formulations, commonly used non-toxic carriers include, but are not limited to, mannitol, lactose, starch, magnesium stearate, cellulose, glucose, sucrose, etc. Carriers for use in liquid formulations include, but are not limited to, water, physiological saline, a solution of glucose in water, ethylene glycol, polyethylene glycol, etc. The active compound can form a solution or suspension with the above carrier. The specific mode of administration and dosage form depend on the physicochemical properties of the compound per se, the severity of the disease to be treated, etc. Those skilled in the art can determine the specific route of administration based on the above considerations in combination with their own knowledge. See, for example, Jun Li, "Clinical Pharmacology", People's Medical Publishing House, June 2008; Yufeng Ding, Discussion on considerations of clinical dosage forms and rational drug use, Herald of Medical, 26 (5), 2007; Howard C. Ansel, Loyd V. Allen, Jr., Nicholas G. Popovich (ed.), Zhiqiang Jiang (primary translator), "Pharmaceutical Dosage Forms and Delivery Systems", China Medical Science Press, May 2003.

The pharmaceutical composition of the present invention can be present in a unit dosage form containing a predetermined amount of the active ingredient per unit dose. Preferred unit dose compositions are those containing a daily dose or sub-dose, or an appropriate fraction of the active ingredient. Therefore, such a unit dose can be administered more than once a day. Preferred unit dose compositions are those containing the daily or sub-dose as described herein-above (administered more than once a day), or an appropriate fraction of the active ingredient.

The pharmaceutical composition of the present invention is formulated, quantified, and administered in a manner consistent with criteria in medical practice. The "therapeutically effective amount" of the compound of the present invention is determined by factors such as the specific disorder to be treated, the individual to be treated, the cause of the disorder, the target of the drug, and the mode of administration. Generally, the dosage for parenteral administration can be 1-200 mg/kg/day, and the dosage for oral administration can be 1-1000 mg/kg/day.

The ranges of effective doses as provided herein are not intended to limit the scope of the present invention, but represent preferred dose ranges. However, the most preferred dosage can be adjusted for individuals, which is understood and determinable by those skilled in the art (see, for example, Berkow, et al., Merck Manuals, 16th Edition, Merck, Rahway, N.J., 1992).

In one embodiment, the present invention provides use of the 5-aminopyrazole carboxamide compound as shown in Formula (I) and crystalline form I thereof in the manufacture of a medicament for preventing or treating diseases mediated by BTK.

The present invention provides a method for inhibiting BTK activity, comprising administering to a biological system the 5-aminopyrazole carboxamide compound as shown in Formula (I) or crystalline form I thereof according to the present invention, or a pharmaceutical composition comprising the 5-aminopyrazole carboxamide compound as shown in Formula (I) or crystalline form I thereof according to the present invention.

In some embodiments, the biological system is an enzyme, cell, or mammal.

In one embodiment, the present invention also provides a method for preventing or treating a disease mediated by BTK, comprising administering to a patient in need thereof a therapeutically effective dose of the 5-aminopyrazole carboxamide compound as shown in Formula (I) or crystalline form I thereof according to the present invention in combination with one or more agents selected from the group consisting of immunomodulators, immune checkpoint inhibitors, glucocorticoids, non-steroidal anti-inflammatory drugs, specific Cox-2 Inhibitors, TNF-α binding proteins, interferons, interleukins, and chemotherapeutic agents.

In embodiments of the present invention, the disease mediated by BTK includes an autoimmune disease, an inflammatory disease, a xenoimmune condition or disease, a thromboembolic disease, and a cancer. In some specific embodiments, the cancer includes B-cell chronic lymphocytic leukemia, acute lymphocytic leukemia, non-Hodgkin's lymphoma, Hodgkin's lymphoma, acute myeloid leukemia, diffuse large B-cell lymphoma, multiple myeloma, mantle cell lymphoma, small lymphocytic lymphoma, Waldenström macroglobulinemia, and a solid tumor. In some particular embodiments, the autoimmune disease and inflammatory disease are selected from the group consisting of rheumatoid arthritis, osteoarthritis, juvenile arthritis, chronic obstructive pulmonary disease, multiple sclerosis, systemic lupus erythematosus, psoriasis, psoriatic arthritis, Crohn's disease, ulcerative colitis, and irritable bowel syndrome. In some particular embodiments, the xenoimmune condition or disease includes a graft-versus-host disease, transplantation, blood transfusion, anaphylaxis, allergy, type I hypersensitivity, allergic conjunctivitis, allergic rhinitis, or atopic dermatitis.

Experimental data proves that the 5-aminopyrazole carboxamide compound as shown in Formula (I) and the crystalline form thereof as provided in the present invention are effective and safe inhibitors of the protein kinase BTK.

DETAILED DESCRIPTION OF THE INVENTION

Figure 1:
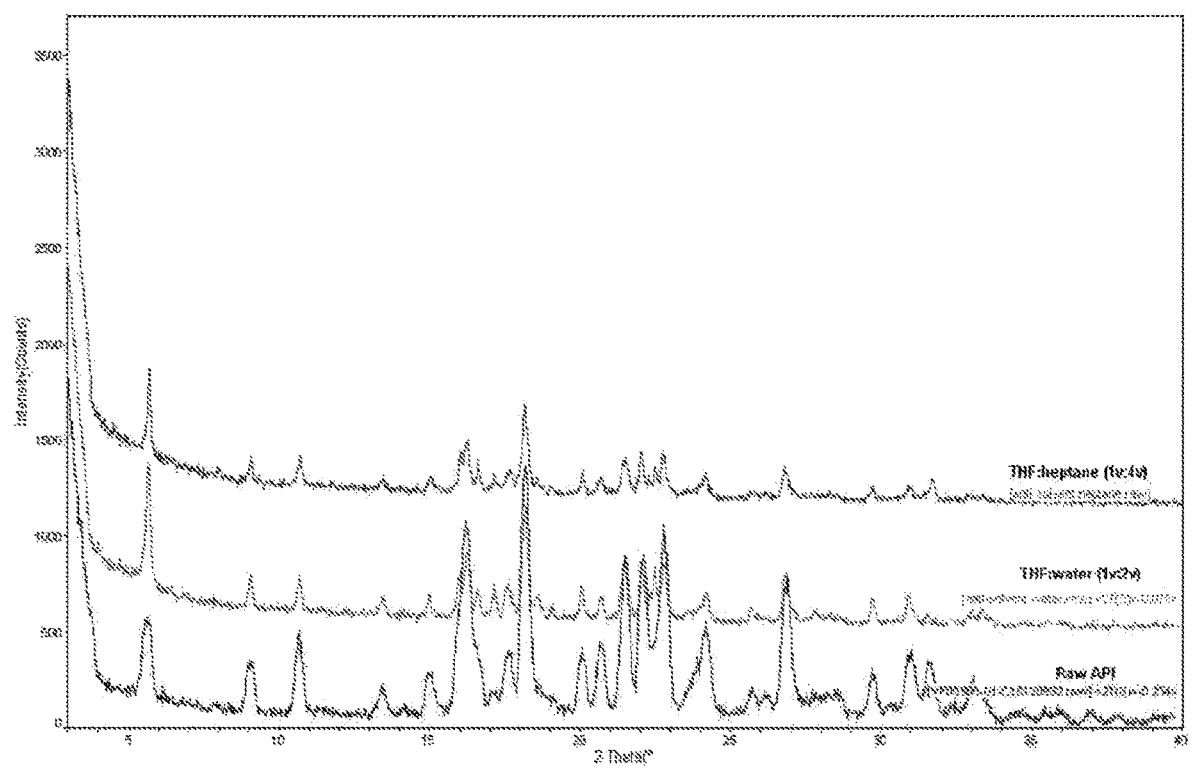
FIG. 1 shows an X-ray powder diffraction pattern of crystalline form I of the compound of the present invention prepared in different solvents.

The experiments, synthetic methods and intermediates as described below are only illustrative for the present invention, and not intended to limit the scope of the present invention.

The starting materials used in the experiments of the present invention were either purchased from reagent suppliers or prepared from known raw materials by methods well-known in the art. Unless otherwise stated, the following conditions apply to the Examples herein:

The unit of temperatures is Celsius (° C.); and room temperature is defined as 18-25° C.;

The organic solvents were dried over anhydrous magnesium sulfate or anhydrous sodium sulfate; and spin-dried under reduced pressure at an elevated temperature on a rotary evaporator (e.g., 15 mmHg, 30° C.);

200-300 mesh silica gel was used as a carrier in column chromatography;

Generally, the progress of the reactions was monitored by thin layer chromatography or LC-MS;

The identification of the final products was completed by nuclear magnetic resonance (Bruker AVANCE 300, 300 MHz) and LC-MS (Bruker esquine 6000, Agilent 1200 series).

EXAMPLE 1

Preparation of 5-amino-3-(4-((5-chloropyridin-2-yl)oxy)phenyl)-1-(4-cyano-4-azaspiro[2.5]oct-6-yl)-1H-pyrazole-4-carboxamide (II)

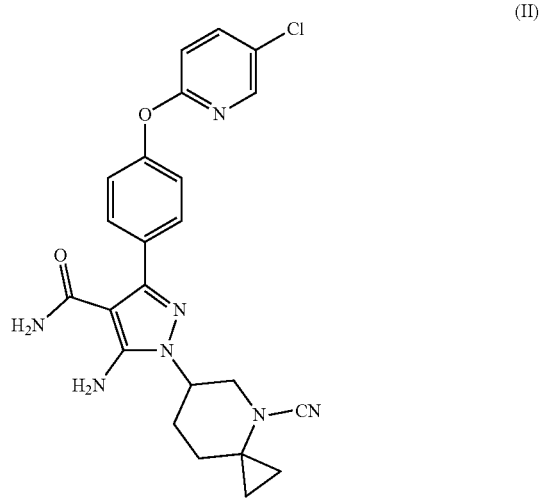 [SMILES: N#CN1CC(n2nc(-c3ccc(Oc4ccc(Cl)cn4)cc3)c(C(N)=O)c2N)CCC12CC2]

(II)

Step 1. Preparation of methyl 4-hydroxybutyrate

Dihydrofuran-2(3H)-one (100 g, 1.163 mol) and triethylamine (460 g, 4.65 mol) were added to a methanol solution (1 L), and the reaction was reacted at 60° C. for 24 hours. Thin layer chromatography (petroleum ether:ethyl acetate=2:1) was used to detect the completion of reaction, and the reaction solution was spin-dried to afford methyl 4-hydroxybutyrate (120 g, 87.6%, as a yellow liquid) which was directly used in the next step.

Step 2. Preparation of methyl 4-oxobutyrate

Methyl 4-hydroxybutyrate (120 g, 1.02 mol) was added to a dichloromethane solution (1.2 L), then pyridinium chlorochromate (330 g, 1.53 mol) was added to the above reaction solution, and the reaction was carried out at room temperature for 12 hours. Thin layer chromatography (petroleum ether:ethyl acetate=3:1) was used to detect that the reaction was completed. The reaction solution was filtered through celite and spin-dried to give methyl 4-oxobutyrate (60 g, 50%, as a yellow liquid), which was used directly in the next step.

Step 3. Preparation of methyl 4-hydroxy-5-nitrovalerate

In an ice water bath, methyl 4-oxobutyrate (60 g, 0.46 mol), nitromethane (42 g, 0.69 mol), tetrahydrofuran (300 mL), and tert-butanol (300 mL) were added to a reaction flask. Then potassium tert-butoxide (5 g) was slowly added to the above reaction system, the temperature was raised to room temperature, and the reaction was carried out for 2 hours. Thin layer chromatography (petroleum ether:ethyl acetate=3:1) was used to detect that the reaction was completed, and water (30 mL) was added to quench the reaction. The solvent was spin-dried. Water (300 mL) and ethyl acetate (300 mL) were added for liquid separation. The organic phase was washed with saturated brine, dried over anhydrous sodium sulfate, and spin-dried to give crude methyl 4-hydroxy-5-nitrovalerate (45 g, as a pale yellow oily liquid), which was used directly in the next step.

Step 4. Preparation of 5-hydroxypiperidin-2-one

Methyl 4-hydroxy-5-nitrovalerate (45 g, 0.23 mol) and palladium on carbon (2.1 g) were added to a methanol solution (500 mL), and the reaction solution was reacted at 60° C. under $H_2$ for 24 hours. Thin layer chromatography (petroleum ether:ethyl acetate=1:1) was used to detect the completion of reaction. The reaction solution was filtered through celite, and the filtrate was spin-dried to give 5-hydroxypiperidin-2-one (10 g, as a yellow solid, 38%), which was used directly in the next reaction.

Step 5. Preparation of 1-benzyl-5-(benzyloxy)piperidin-2-one 5-hydroxypiperidin-2-one (10 g, 0.1 mol) was added to dimethyl sulfoxide (100 mL) at room temperature, and then sodium hydride (10 g, 0.25 mol) was slowly added to the above reaction system. After the completion of addition, benzyl bromide (43.5 g, 0.25 mol) was added to the reaction solution, and stirred overnight. Thin layer chromatography (petroleum ether:ethyl acetate=1:1) was used to detect that the reaction was completed. To the reaction system was added saturated aq. ammonium chloride (100 mL) to quench the reaction. The reaction was extracted with EtOAc three times (100 mL*3), washed with saturated brine, dried over anhydrous sodium sulfate, spin-dried, and purified by column chromatography to yield 1-benzyl-5-(benzyloxy)piperidin-2-one (16 g, as a yellow solid, 54%).

Step 6. Preparation of 4-benzyl-6-(benzyloxy)-4-azaspiro[2.5]octane 1-benzyl-5-(benzyloxy)piperidin-2-one (15 g, 50 mmol) was dissolved in anhydrous tetrahydrofuran (150 mL) under protection of a nitrogen atmosphere at −78° C., then ethyl magnesium bromide (150 mL) was slowly added to the reaction flask dropwise. After the dropping process was completed, tetrapropyl titanate (45 g, 150 mmol) was added to the above reaction system. After the addition was completed, the reaction was warmed to room temperature and stirred for 2 hours. Thin layer chromatography (petroleum ether:ethyl acetate=10:1) was used to detect that the reaction was completed. The reaction was quenched by addition of saturated aq. ammonium chloride (100 ml) to the reaction system, extracted with ethyl acetate three times (100 mL*3). The combined organic phase was washed with saturated brine, dried over anhydrous sodium sulfate, spin-dried, and purified by column chromatography to yield 4-benzyl-6-(benzyloxy)-4-azaspiro[2.5]octane (5.1 g, as a yellow solid, 31%).

Step 7. Preparation of 4-azaspiro[2.5]oct-6-ol 4-benzyl-6-(benzyloxy)-4-azaspiro[2.5]octane (5.5 g, 18 mmol) and palladium on carbon (2 g, 1.8 mmol) were added to a solution of methanol (200 mL) and hydrogen chloride (2 mL). The reaction solution was reacted under $H_2$ at 60° C. for 48 hours. Thin layer chromatography (petroleum ether:ethyl acetate=10:1) was used to detect that the reaction was completed. The reaction solution was filtered through celite, and the filtrate was spin-dried to yield 4-azaspiro[2.5]oct-6-ol (2.5 g, as a yellow solid), which was used directly in the next step.

Step 8. Preparation of benzyl 6-hydroxy-4-azaspiro[2.5]octane-4-carboxylate

4-Azaspiro[2.5]oct-6-ol (2.5 g, 21 mmol) and sodium bicarbonate (3.8 g, 45 mmol) were added to a solution of tetrahydrofuran (100 mL), then benzyloxycarbonyl chloride (4.25 g, 25 mmol) was added dropwise to the above reaction system. The reaction solution was reacted at room temperature for 48 hours. Thin layer chromatography (petroleum ether:ethyl acetate=3:1) was used to detect that the reaction was completed. The reaction solution was filtered, and the filtrate was spin-dried and purified by column chromatography to yield benzyl 6-hydroxy-4-azaspiro [2.5] octane-4-carboxylate (4.2 g).

Step 9. Preparation of benzyl 6-oxo-4-azaspiro[2.5]octane-4-carboxylate

Benzyl 6-hydroxy-4-azaspiro[2.5]octane-4-carboxylate (4.2 g, 16 mmol) and 2-iodoxybenzoic acid (6.7 g, 24 mmol) were added to acetone (100 mL). Then the reaction solution was warmed to 60° C. to react for 12 hours. Thin layer chromatography (petroleum ether:ethyl acetate=2:1) was used to detect that the reaction was completed, and the reaction solution was extracted, the filtrate was spin-dried and purified by the column chromatography to yield benzyl 6-oxo-4-azaspiro[2.5]octane-4-carboxylate (3.6 g, 85%).

1H-NMR (400 MHz, DMSO-d6): δ ppm 7.34-7.35 (m, 5H), 5.15 (s, 2H), 4.07 (s, 2H), 2.55-2.58 (m, 2H), 1.95-1.98 (m, 2H), 1.09-1.11 (m, 2H), 0.85-0.86 (m, 2H).

Step 10. Preparation of benzyl (E)-6-(2-(tert-butoxycarbonyl)hydrazono)-4-azaspiro[2.5]octane-4-carboxylate Benzyl 6-oxo-4-azaspiro[2.5]octane-4-carboxylate (3.6 g, 13.9 mmol) and tert-butoxycarbonyl hydrazine (1.98 g, 15 mmol) were added to tetrahydrofuran (50 mL). The reaction solution was warmed to 70° C. to react for 2 hours. Thin layer chromatography (petroleum ether:ethyl acetate=2:1) was used to detect that the reaction was completed. The reaction solution was extracted, and the filtrate was spin-dried and purified by column chromatography to give benzyl (E) -6-(2-(tert-butoxycarbonyl)hydrazono)-4-azaspiro[2.5] octane-4-carboxylate (5.0 g, 90%).

Step 11. Preparation of benzyl 6-(2-(tert-butoxycarbonyl)hydrazino)-4-azaspiro [2.5]octane-4-carboxylate Benzyl (E)-6-(2-(tert-Butoxycarbonyl)hydrazono)-4-azaspiro[2.5]octane-4-carboxylate (5.0 g, 13.4 mmol) and sodium cyanoborohydride (1.4 g, 20 mmol) were added to tetrahydrofuran (100 mL), then p-toluenesulfonic acid (3.8 g, 20 mmol) was added dropwise to the above reaction system. The reaction solution was allowed to react at room temperature for 36 hours. Thin layer chromatography (petroleum ether:ethyl acetate=1:1) was used to detect that the reaction was completed. The reaction solution was extracted, and the filtrate was spin-dried and purified by column chromatography to give benzyl 6-(2-(tert-butoxycarbonyl)hydrazino)-4-azaspiro[2.5]octane-4-carboxylate (4.2 g, 80.4%).

Step 12. Preparation of benzyl 6-hydrazino-4-azaspiro[2.5]octane-4-carboxylate

Benzyl 6-(2-(tert-butoxycarbonyl)hydrazino)-4-azaspiro[2.5]octane-4-carboxylate (4.2 g, 11 mmol) was added to a solution of hydrogen chloride/ethyl acetate (50 mL). The reaction was carried out at room temperature for 12 hours, and thin layer chromatography (petroleum ether:ethyl acetate=2:1) was used to detect that the reaction was completed. The reaction solution was extracted, and the filtrate was spin-dried and purified by column chromatography to yield benzyl 6-hydrazino-4-azaspiro[2.5]octane-4-carboxylate (3.5 g).

1H-NMR (400 MHz, DMSO-d6): δ ppm 7.21-7.35 (m, 10H), 4.46-4.54 (m, 2H), 3.89-3.93 (m, 1H), 3.78-3.81 (m, 1H), 3.68-3.73 (m, 1H), 2.86-2.90 (m, 1H), 2.63-2.68 (m, 1H), 2.08-2.12 (m, 1H), 1.57-1.85 (m, 2H), 1.24-1.29 (m, 1H), 0.65 (s, 2H). 0.41-0.44 (m, 2H)

Step 13. Preparation of methyl 4-((5-chloropyridin-2-yl)oxy)benzoate

Methyl 4-hydroxybenzoate (6.5 g, 49 mmol), 5-chloro-2-fluoropyridine (5.0 g, 33 mmol) and cesium carbonate (20 g, 65 mmol) were dissolved in N,N-dimethyl formamide (50 mL) with stirring. The reaction solution was refluxed at 110° C. for 12 hours. Thin layer chromatography (petroleum ether:ethyl acetate=5:1) was used to detect that the reaction was completed, and the solvent was spin-dried. The crude compound was partitioned between ethyl acetate (250 mL) and water (250 mL). The organic phase was dried over anhydrous sodium sulfate, filtered and evaporated to dryness under reduced pressure. The crude compound was purified by column chromatography to yield the product methyl 4-((5-chloropyridin-2-yl)oxy)benzoate (9.0 g, 93%).

MS: m/z 264.2 [M+1]

Step 14. Preparation of 4-((5-chloropyridin-2-yl)oxy)benzoic acid

Methyl 4-((5-chloropyridin-2-yl)oxy)benzoate (6.5 g, 49 mmol) was dissolved in methanol (100 mL) and water (5 mL). Lithium hydroxide (2.3 g) was then added to the reaction system with stirring. The reaction solution was reacted at 45° C. for 12 hours. Thin layer chromatography (petroleum ether:ethyl acetate=1:1) was used to detect that the reaction was completed. The solvent was spin-dried. To the crude compound was added diluted aq. hydrochloric acid (100 mL, 1 M) to pH=7. At this time, a substantial amount of solids was generated, and the solids were filtered and oven-dried to give the product 4-((5-chloropyridin-2-yl)oxy)benzoic acid (6.5 g, as a white solid, 84%).

MS: m/z 250.1 [M+1]

Step 15. Preparation of 4-((5-chloropyridin-2-yl)oxy)benzoyl chloride 4-((5-Chloropyridin-2-yl)oxy)benzoic acid (6.5 g, 23 mmol) was added to dichlorosulfoxide (20 mL), and the reaction solution was reacted at 80° C. for 3 hours. Thin layer chromatography (petroleum ether:ethyl acetate=3:1) was used to detect that the reaction was completed. The solvent was spin-dried and the crude product 4-((5-chloropyridin-2-yl)oxy)benzoyl chloride (7 g, as a yellow solid) was used directly in the next step.

Step 16. Preparation of 2-((4-((5-chloropyridin-2-yl)oxy)phenyl)(hydroxy)methylene)malononitrile Malononitrile (3.72 g, 56.4 mmol) was dissolved in anhydrous tetrahydrofuran (50 mL) at 0° C., and then sodium hydride (3.6 g, 90 mmol, 60%) was slowly added. After the addition is completed, the reaction was warmed to room temperature and stirred for 1 hour, and then cooled to 0° C. 4-((5-chloropyridin-2-yl)oxy)benzoyl chloride (6 g, 22.2 mmol) dissolved in anhydrous tetrahydrofuran (50 mL) was slowly added to the above reaction solution dropwise. After the dropping process was completed, the reaction solution was stirred at 0° C. for 1 hour. Thin layer chromatography (petroleum ether:ethyl acetate=3:1) was used to detect the completion of reaction, and a new spot was generated. The reaction solution was quenched with saturated aq. ammonium chloride (100 mL), extracted with EtOAc three times (100 mL*3). The organic phase was washed with saturated brine (100 mL), dried over anhydrous sodium sulfate, and spin-dried. The crude compound was mashed with petroleum ether:ethyl acetate=50:1 to give 2-((4-((5-chloropyridin-2-yl)oxy)phenyl)(hydroxy)methylene)malononitrile (8.0 g, as a pale yellow solid, 82%).

MS: m/z 298 [M+1]

Step 17. Preparation of 2-((4-((5-chloropyridin-2-yl)oxy)phenyl)(ethoxy)methylene)malononitrile 2-((4-((5-chloropyridin-2-yl)oxy)phenyl)(hydroxy)methylene)malononitrile (5.0 g, 16.8 mmol) was added to triethyl orthoformate (50 mL). The reaction was warmed to 80° C. and stirred for 12 hours. Thin layer chromatography (petroleum ether:ethyl acetate=3:1) indicated that a product was produced. The reaction solution was filtered, and the filtrate was spin-dried. The resulting solid was mashed with methanol to give 2-((4-((5-chloropyridin-2-yl)oxy)phenyl)(ethoxy)methylene)malononitrile (1.5 g, as a white product, 27.7%).

MS: m/z 326.0 [M+1]

Step 18. Preparation of benzyl 6-(5-amino-3-(4-((5-chloropyridin-2-yl)oxy)phenyl)-4-cyano-1H-pyrazol-1-yl)-4-azaspiro[2.5]octane-4-carboxylate 2-((4-((5-chloropyridin-2-yl)oxy)phenyl)(ethoxy)methylene)malononitrile (1.0 g, 3.09 mmol), benzyl 6-hydrazino-4-azaspiro[2.5]octane-4-carboxylate (1.28 g, 3.71 mmol) and triethylamine (1.56 g, 15.5 mmol) were dissolved in ethanol (20 mL). The reaction solution was reacted at 25° C. for 12 hours, and thin layer chromatography (petroleum ether:ethyl acetate=2:1) was used to detect that the reaction was completed. The reaction was quenched with addition of water, and extracted with ethyl acetate (25 mL*3). The organic phase was dried over anhydrous sodium sulfate, filtered and spin-dried. The crude compound was mashed twice with petroleum ether:ethyl acetate=50:1 to give the product benzyl 6-(5-amino-3-(4-((5-chloropyridin-2-yl)oxy)phenyl)-4-cyano-1H-pyrazol-1-yl)-4-azaspiro[2.5]octane-4-carboxylate (1.5 g, 88%).

MS: m/z 555.2 [M+1]

Step 19. Preparation of 5-amino-3-(4-((5-chloropyridin-2-yl)oxy)phenyl)-1-(4-azaspiro [2.5]oct-6-yl)-1H-pyrazole-4-carboxamide Benzyl 6-(5-amino-3-(4-((5-chloropyridin-2-yl)oxy)phenyl)-4-cyano-1H-pyrazol-1-yl)-4-azaspiro[2.5]octane-4-carboxylate (750 mg, 1.35 mmol) was added to 90% concentrated sulfuric acid (over 10 min) at room temperature, and stirred for 15 minutes, then the reaction system was warmed to 30° C. to react for 24 hours. Thin layer chromatography (dichloromethane:methanol=10:1) was used to detect that the reaction was completed. The reaction solution was slowly poured into aqueous ammonia (50 ml) and adjusted to pH=7, and extracted with ethyl acetate three times (30 mL*3). The combined organic phase was washed with saturated brine (30 mL), dried over anhydrous sodium sulfate, and spin-dried. The crude compound was purified by column chromatography to yield 5-amino-3-(4-((5-chloropyridin-2-yl)oxy)phenyl)-1-(4-azaspiro[2.5]oct-6-yl)-1H-pyrazole-4-carboxamide (480 mg, 78%, as a pale yellow solid).

MS: m/z 439.2 [M+1]

Step 20. Preparation of 5-amino-3-(4-((5-chloropyridin-2-yl)oxy)phenyl)-1-(4-cyano-4-azaspiro[2.5]oct-6-yl)-1H-pyrazole-4-carboxamide 5-amino-3-(4-((5-chloropyridin-2-yl)oxy)phenyl)-1-(4-azaspiro[2.5]oct-6-yl)-1H-pyrazole-4-carboxamide (50 mg, 0.113 mmol) was dissolved in N,N-dimethylformamide (5 mL), then cesium carbonate (110 mg, 0.342 mmol) and cyanogen bromide (12.5 mg, 0.113 mmol) were added. The reaction solution was stirred at room temperature for 2 hours, and then subjected to thin layer chromatography to detect that the reaction was completed. The reaction solution was poured into ethyl acetate (50 mL) and washed with water (20 mL*3), dried over anhydrous sodium sulfate, filtered and evaporated to dryness under a reduced pressure. The crude product was purified by a preparative thin layer chromatography (dichloromethane:methanol=50:1) to give the product 5-amino-3-(4-((5-chloropyridin-2-yl)oxy)phenyl)-1-(4-cyano-4-azaspiro[2.5]oct-6-yl)-1H-pyrazole-4-carboxamide (15 mg, 15%).

$^1$H-NMR (400 MHz, DMSO-d6): δ ppm 8.12 (s, 1H), 7.66-7.69 (dd, $J_1$=2.4 Hz, $J_2$=8.4 Hz 2H), 7.56-7.58 (d, J=8 Hz, 2H), 7.21-7.23 (d, J=8 Hz, 2H), 6.92-6.94 (d, J=8 Hz, 1H), 5.61 (s, 1H), 5.19-5.30 (m, 2H), 4.19-4.25 (m, 1H), 3.52-3.66 (m, 2H), 2.34-2.45 (m, 2H), 2.19 (s, 1H), 1.25-1.30 (m, 1H), 1.15-1.20 (m, 1H), 0.78-0.89 (m, 2H), 0.66-0.71 (m, 1H).

MS: m/z 446.2 [M+1]

EXAMPLE 2

Preparation of (R)-5-amino-3-(4-((5-chloropyridin-2-yl)oxy)phenyl)-1-(4-cyano-4-azaspiro[2.5]octan-6-yl)-1H-pyrazole-4-carboxamide (I) and (S)-5-amino-3-(4-((5-chloropyridin-2-yl)oxy)phenyl)-1-(4-cyano-4-azaspiro[2.5]octan-6-yl)-1H-pyrazole-4-carboxamide (III)

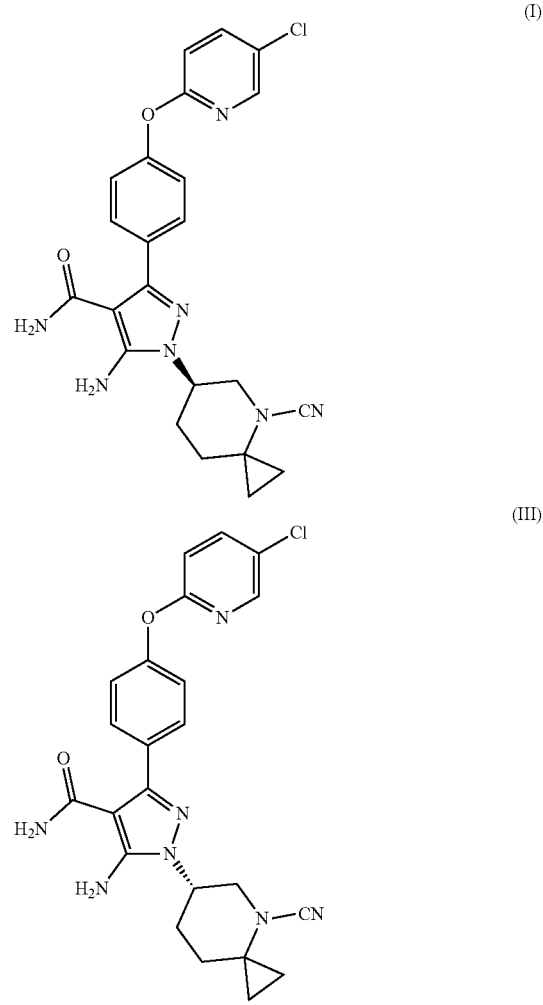

After chiral resolution of the product of Example 1, the compounds of Example 2 could be obtained. The conditions for the resolution were as follows: Supercritical fluid chromatography (ChiralPak AD 5 μ, 21×250 mm col, 27% methanol, 70 mL/min).

The spectral data of the compound (R)-5-amino-3-(4-((5-chloropyridin-2-yl)oxy)phenyl)-1-(4-cyano-4-azaspiro[2.5]octan-6-yl)-1H-pyrazole-4-carboxamide (I):

$^1$H-NMR (400 MHz, CDCl3): δ ppm 8.12 (s, 1H), 7.69-7.67 (m, 1H), 7.57 (d, J=8.4 Hz, 2H), 7.22 (d, J=8.4 Hz, 2H), 6.93 (d, J=8.8 Hz, 1H), 5.60 (s, 2H), 5.24 (s, 2H), 4.25-4.20 (m, 1H), 3.67-3.48 (m, 2H), 2.42-2.35 (m, 2H), 2.19-2.16 (m, 1H), 1.30-1.26 (m, 1H), 1.21-1.16 (m, 1H), 0.90-0.79 (m, 2H), 0.71-0.67 (m, 1H).

MS: m/z 464.4 [M+H]

The spectral data of the compound (S)-5-amino-3-(4-((5-chloropyridin-2-yl)oxy)phenyl)-1-(4-cyano-4-azaspiro[2.5]oct-6-yl)-1H-pyrazole-4-carboxamide (III):

$^1$H-NMR (400 MHz, CDCl3): δ ppm 8.12 (s, 1H), 7.69-7.67 (m, 1H), 7.57 (d, J=8.4 Hz, 2H), 7.22 (d, J=8.4 Hz, 2H), 6.93 (d, J=8.8 Hz, 1H), 5.60 (s, 2H), 5.24 (s, 2H), 4.25-4.20 (m, 1H), 3.67-3.48 (m, 2H), 2.42-2.35 (m, 2H), 2.19-2.16 (m, 1H), 1.30-1.26 (m, 1H), 1.21-1.16 (m, 1H), 0.90-0.79 (m, 2H), 0.71-0.67 (m, 1H).

MS: m/z 464.4 [M+H]

EXAMPLE 3

Preparation of crystalline form I of (R)-5-amino-3-(4-((5-chloropyridin-2-yl)oxy)phenyl)-1-(4-cyano-4-azaspiro[2.5]oct-6-yl)-1H-pyrazole-4-carboxamide (I)

About 20 mg of the compound of Formula (I) was dissolved in 1 mL of tetrahydrofuran, and water was added to the resulting solution, in which the volume ratio of tetrahydrofuran to water was 1:2. The resulting suspension was stirred at 25° C. for 24 h, and then separated by centrifugation. The resulting solid was dried under vacuum at 30° C. for about 3 h to afford yellow crystalline form I of the compound of Formula (I).

X-ray powder diffraction analysis of the above crystalline form I:

About 10 mg of the sample was uniformly dispersed onto a single crystal silicon plate for XRPD detection. Specific instrument parameters were as follows:
Light tube: Cu: K-Alpha (λ=1.54179 Å)
Light tube voltage: 40 kV
Light tube current: 40 mA
Scanning range: 3-40 deg.
Sample tray speed: 15 rpm
Scanning rate: 10 deg./min Finally, an X-ray powder diffraction pattern of the above crystalline form I was obtained, as shown in FIG. 1.

EXAMPLE 4

Preparation of crystalline form I of (R)-5-amino-3-(4-((5-chloropyridin-2-yl)oxy)phenyl)-1-(4-cyano-4-azaspiro[2.5]oct-6-yl)-1H-pyrazole-4-carboxamide (I)

About 20 mg of the compound of Formula (I) was dissolved in 1 mL of tetrahydrofuran, and n-heptane was added to the resulting solution, in which the volume ratio of tetrahydrofuran to n-heptane was 1:4. The resulting suspension was stirred at 25° C. for 24 h, and then separated by centrifugation. The resulting solid was dried under vacuum at 30° C. for about 3 h to afford yellow crystalline form I of the compound of Formula (I).

An X-ray powder diffraction analysis was performed on the obtained crystalline form I by a method similar to that in Example 3, to obtain an X-ray powder diffraction pattern substantially the same as that of the crystalline form I obtained in Example 3, as shown in FIG. 1.

EXAMPLE 5

Kinase Activity (BTK) Inhibition Assay

The inhibitory effects of compound (R)-5-amino-3-(4-((5-chloropyridin-2-yl)oxy)phenyl)-1-(4-cyano-4-azaspiro[2.5]oct-6-yl)-1H-pyrazole-4-carboxamide (I) on BTK kinase activity were tested in an assay based on a time resolved fluorescence resonance energy transfer (TR-FRET) method. Recombinant Btk was pre-incubated with the compound disclosed herein in an assay buffer containing 50 mM Tris pH 7.4, 10 mM MgCl$_2$, 2 mM MnCl$_2$, 0.1 mM EDTA, 1 mM DTT, 20 nM SEB, 0.1% BSA, 0.005% tween-20 at room temperature for 1 hour. The reaction was initiated by the addition of ATP (at the ATP Km concentration) and the peptide substrate (Biotin-AVLESEEELYSSARQ-NH$_2$). After incubation at room temperature for 1 hour, an equal volume of stop solution containing 50 mM HEPES pH 7.0, 800 mM KF, 20 mM EDTA, 0.1% BSA, p-Tyr66 antibody linked with Eu cryptate and streptavidin-labeled XL665 was added to stop the reaction. The plate was incubated at room temperature for an additional hour and then the TR-FRET signal was read on a BMG PHERAstar FS instrument (ex337 nm, em 620 nm/665 nm). Based on the ratio of the signal of fluorescence at 615 nm to 665 nm, the residual enzyme activity was calculated with an increased compound concentration. IC50 of each compound was obtained by fitting the data to the four-parameter equation of Graphpad Prism software.

According to the above experimental method, the compound (R)-5-amino-3-(4-((5-chloropyridin-2-yl) oxy)phenyl)-1-(4-cyano-4-azaspiro[2.5]oct-6-yl)-1H-pyrazole-4-carboxamide (I) exhibits strong inhibitory effect on kinase (IC50<100 nM).

EXAMPLE 6

In Vitro Kinase Selectivity Assay

The assay platform for EGFR and ITK kinase activities was established using time-resolved fluorescence resonance energy transfer-based method; the assay platform for LCK, SRC and LYN kinase activities was established using Z'-Lyte method; and the assay platform for TEC and JAK3 kinase activities was established using Lance Ultra method. The inhibitory effects of the compounds disclosed herein on different kinase activities were tested separately for each compound at 11 concentrations. The IC50 value of the compound was calculated using Graphpad Prism software.

According to the above experimental methods, compound (R)-5-amino-3-(4-((5-chloropyridin-2-yl)oxy)phenyl)-1-(4-cyano-4-azaspiro[2.5]oct-6-yl)-1H-pyrazole-4-carboxamide (I) exhibits very high kinase selectivity profile, which was significantly better than that of the control compound ibrutinib. See the table below for the results.

| Compound No. | LCK | SRC | LYN | EGFR | ITK | TEC |
|---|---|---|---|---|---|---|
| Compound I | C | C | C | B | C | A |
| ibrutinib | A | A | A | A | A | A |

The kinase inhibitory activity grades are assigned to A, B, and C, specifically, A (IC$_{50}$<100 nM), B (100 nM<IC$_{50}$<1000 nM), C (IC$_{50}$>1000 nM).

EXAMPLE 7

B Cell Inhibition Assay

Temporary exposure to a BTK inhibitor in vitro is sufficient to inhibit B cell activation in normal human B cells. This protocol mimics the predicted exposure of cells to the inhibitor in vivo, and shows that the inhibition of B cells is maintained even when the inhibitor was washed off.

B cells were obtained by purification from healthy donor blood through negative selection using the RosetteSep human B Cell Enrichment Mix. Cells were plated in a growth medium (10% RPMI+10% fetal bovine serum) and the inhibitor was added at specified concentrations. After incubation at 37° C. for 1 hour, the cells were washed three times, and each wash was used for 8-fold dilution in the growth medium. The cells were then stimulated with 10 µg/mL IgM F(ab')2 at 37° C. for 18 hours. Cells were subsequently stained with an anti-CD69-PE antibody and analyzed by flow cytometry using standard conditions.

According to the above experimental methods, compound (R)-5-amino-3-(4-((5-chloropyridin-2-yl)oxy)phenyl)-1-(4-cyano-4-azaspiro[2.5]oct-6-yl)-1H-pyrazole-4-carboxamide (I) has strong inhibitory activities on B cells with an $IC_{50}$ less than 10 nM.

EXAMPLE 8

T Cell Inhibition Assay

T cells were obtained by purification of healthy donor blood through negative selections using the RosetteSep Human T Cell Enrichment Mix. Cells were plated in a growth medium (10% RPMI+10% fetal bovine serum) and the inhibitor was added at specified concentrations. After incubating for 1 hour at 37° C., the cells were washed three times, and each wash was used for 10-fold dilution in the growth medium. The cells were then stimulated with anti-CD3/CD28 coated beads (bead/cell ratio 1:1) for 18 hours at 37° C. Cells were subsequently stained with an anti-CD69-PE antibody and analyzed by flow cytometry using standard conditions. According to the above experimental methods, compound (R)-5-amino-3-(4-((5-chloropyridin-2-yl)oxy)phenyl)-1-(4-cyano-4-azaspiro[2.5]oct-6-yl)-1H-pyrazole-4-carboxamide (I) has very low or no inhibitory activity on T cells, with an $IC_{50}$ values higher than 4000 nM.

EXAMPLE 9

Inhibition Assay on Human Whole Blood B Cells

Human whole blood (hWB) was obtained from healthy volunteers and blood was collected by venipuncture into a heparin sodium-anticoagulant Vacutainer tube. Test compounds were diluted 10 times in PBS to the required initial drug concentration), followed by three-fold serial dilutions with 10% DMSO in PBS to obtain a 9-point dose response curve. 5.5 µL of each diluted compound was added to the aiiI 96-well V-bottom plate in duplicate; 5.5 µL of 10% DMSO in PBS was added to control and non-stimulated wells. Human whole blood (100 µL) was added to each well, and after mixing, the plates were incubated for 30 minutes at 37° C. and in 5% $CO_2$, 100% humidity. An anti-human IgM F(ab')2 (Southern Biotech) (10 µL of 500 µg/mL solution, 50 µg/mL final concentration) was added to each well (except for non-stimulated wells) with vortexing, and the plate was further incubated for another 20 hours. After 20-hour incubation, samples were incubated with 20 µL of fluorescent probe-labeled APC mouse anti-human CD69 (BD Pharmingen) for 30 minutes at 37° C., 5% $CO_2$, 100% humidity. Induced controls, unstained, and single-stained samples were included for compensation and initial voltage settings. The samples were then lysed with 1 ml of IX Pharmingen Lyse Buffer (BD Pharmingen) and the plate was centrifuged at 1500 rpm for 5 minutes. The supernatant was removed by aspiration, the remaining pellet was lysed with an additional 1 ml of IX Pharmingen Lyse Buffer, and the plate was centrifuged as above. The supernatant was aspirated off and the remaining pellet was washed in FACs buffer (PBS+1% FBQ). After centrifugation and removal of the supernatant, the pellet was resuspended in 150 µL of FACS buffer. The sample was transferred to a 96-well plate suitable for operating on the HTS 96-well system of the BD LSR II flow cytometer. Data were acquired using the excitation and emission wavelengths suitable for the used fluorophore, and the percent positive cell values were obtained using Cell Quest Software. Results were initially analyzed using FACS analysis software (Flow Jo). The IC50 values were then calculated using XLfit v3, Equation 201.

According to the above experimental methods, compound (R)-5-amino-3-(4-((5-chloropyridin-2-yl)oxy)phenyl)-1-(4-cyano-4-azaspiro[2.5]oct-6-yl)-1H-pyrazole-4-carboxamide (I) has strong inhibitory activities on B cells in human whole blood, with an IC50 value less than 200 nM.

EXAMPLE 10

Stability Study of Compound (R)-5-amino-3-(4-((5-chloropyridin-2-yl)oxy)phenyl)-1-(4-cyano-4-azaspiro[2.5]oct-6- yl)-1H-pyrazole-4-carboxamide (I) in Liver Microsomes 1. Compound (R)-5-amino-3-(4-((5-chloropyridin-2-yl)oxy)phenyl)-1-(4-cyano-4-azaspiro[2.5]oct-6-yl)-1H-pyrazole-4-carboxamide (I) was dissolved in acetonitrile to prepare a stock solution having a concentration of 0.5 mM.

2. 2 µL of stock solution was added to a 1.5 ml centrifuge tube, and then 148 µL of phosphate buffer (100 mM, pH 7.4) and 10 µL of liver microsome suspension (the protein concentration was 20 mg/ml) [BD Gentest] were added. The liver microsomes were derived from the species of human, dog, rat, and mouse; The control group was added with 158 µL of phosphate buffer (100 mM, pH 7.4).

3. The mixture obtained in step 2 was pre-incubated in a 37° C. water bath for 3 minutes; then 40 µL of NADPH generating system (containing NADP+: 6.5 mM, glucose 6-phosphate: 16.5 mM, $MgCl_2$: 16.5 mM, glucose 6-phosphate dehydrogenase: 2 U/ml) was added to initiate the reaction. The reaction system was incubated in a 37° C. water bath for 1 hour.

4. After the reaction was carried out for 1 hour, the centrifuge tube was removed from the water bath, and the reaction was terminated by adding 400 µL of acetonitrile, followed by vortexing for 3 minutes. Finally, the tube was centrifuged (13,000 rpm, 4° C.) for 5 minutes and the supernatant was taken for detection of the remaining drug concentration, Cr, by HPLC.

5. Process for preparing, in parallel, 0-minute reaction sample: the mixture prepared in step 2 was pre-incubated in a 37° C. water bath for 3 minutes. After removing it from the water bath, 400 µL of acetonitrile was added, followed by addition of 40 µL of NADPH generating system. After vortexing for 3 minutes, centrifugation (13,000 rpm, 4° C.) was carried out for 5 minutes. The supernatant was taken for detection of the drug concentration C0 by HPLC.

6. After 60 minutes of incubation, the percentage of remaining drug in the incubation system was calculated as follows:

Remaining Drug (%)=$Cr/C0 \times 100\%$

According to the above experimental method, compound (R)-5-amino-3-(4-((5-chloropyridin-2-yl)oxy)phenyl)-1-(4-cyano-4-azaspiro[2.5]oct-6-yl)-1H-pyrazole-4-carboxamide (I) exhibits improved microsomal stability with a residual percentage >30% in liver microsomes of various species.

EXAMPLE 11

Evaluation of the Compound for Inhibition of CYP Enzyme

CYP enzyme metabolism is a main pathway for drug biotransformation, and the quantity and activity of CYP enzyme directly affect the activation and metabolism of drugs in vivo. As a major metabolic enzyme of exogenous compounds, cytochrome CYP is an important phase I drug metabolic enzyme that can catalyzes the oxidative and reductive metabolism of various exogenous compounds. CYP enzyme plays a very important role in the elimination of drugs, and is also the main factor that causes the drug interactions during a combination drug therapy.

METHOD: This experiment simultaneously determined the inhibitory effects of a compound on five CYP450 enzymes in human liver microsomes using the cocktail probe substrates approach. The human microsomes were from BD Gentest.

The experiment steps are as follows:

The reaction was carried out in 100 mM of phosphate buffer, with a total volume of 200 μL. The concentration of microsomes in the reaction system was 0.25 mg/mL, and the concentration of the test compound was 20 μM, 6.67 μM, 2.22 μM, 0.74 μM, and 0.25 μM. The specific probe substrates and concentration were phenacetin (CYP1A2) 40 μM, dextromethorphan (CYP2D6) 5 μM, diclofenac (CYP2C9) 10 μM, S-mephenytoin (CYP2C19) 40 μM, testosterone (CYP3A4) 80 μM, respectively. The mixture was pre-incubated in a 37° C. thermostatic shaker for 5 minutes, and the NADPH-generating system (containing 1.3 mM NADP+, 3.3 mM glucose 6-phosphate, 0.4 U/L glucose 6-phosphate dehydrogenase, 3.3 mM $MgCl_2$) was added to start the reaction. After incubation for 45 minutes, the reaction was stopped by adding an equal volume of acetonitrile. The tube was vortexed and centrifuged at 13,000 rpm. The resulting supernatant was subjected to LC-MS-MS to determine the amount of produced metabolites. The specific metabolites were acetaminophen (CYP1A2), dextrorphan (CYP2D6), 4-hydroxydiclofenac (CYP2C9), 4-hydroxymefentoin (CYP2C19), and 6β-hydroxytestosterone (CYP3A4), respectively. Specific inhibitors are furaphylline (CYP1A2), quinidine (CYP2D6), sulfaphenazole (CYP2C9), tranylcypromine (CYP2C19), and ketoconazole (CYP3A4), respectively. The final result of this experiment is the calculated half inhibitory concentration IC50 value. IC50=((50%−lowest inhibition percentrage %)/(highest inhibition percentage %−lowest inhibition percentage %))×(highest concentration−lowest concentration)+lowest concentration.

According to the above experimental method, compound (R)-5-amino-3-(4-((5-chloropyridin-2-yl)oxy)phenyl)-1-(4-cyano-4-azaspiro[2.5]oct-6-yl)-1H-pyrazole-4-carboxamide (I) has very low or no inhibitory effect on various CYP enzymes, showing that it has little influence on the metabolism of other drugs.

EXAMPLE 12

Research Method for Pharmacokinetics of Compound (R)-5-amino-3-(4-((5-chloropyridin-2-yl)oxy)phenyl)-1-(4-cyano-4-azaspiro[2.5]oct-6-yl) -1H-pyrazole-4-carboxamide (I) in Rats 1. Male SD rats (HFK) were acclimatized in the laboratory for 7 days after arrival.

2. Nine SD rats were randomly divided into 3 groups, 3 animals in each group. One group was dosed by oral gavage (p.o.), and the other group was dosed by tail vein injection (i.v.). Rats in the p.o. group were fasted overnight before drug administration.

3. After drug administration, blood samples were collected from the rats via the posterior orbital venous plexus approach at the following time points: I.V.: (before drug administration), 0.08 hours, 0.25 hours, 0.5 hours, 1 hour, 2 hours, 4 hours, 8 hours, 24 hours; P.O.: 0.08 hour, 0.25 hour, 0.5 hour, 1 hour, 2 hours, 4 hours, 8 hours, 24 hours. About 300 μl of blood were collected at each collection time point.

4. The collected blood samples were centrifuged at 12000 rpm for 5 minutes at 4° C., and then the upper plasma samples were collected and stored in a refrigerator at −20° C.

5. The experimental operations were summarized in Table 4:

TABLE 4

Design of pharmacokinetics in vivo test of compound (R)-5-amino-3-(4-((5-chloropyridin-2-yl)oxy)phenyl)-1-(4-cyano-4-azaspiro[2.5]oct-6-yl)-1H-pyrazole-4-carboxamide (I) in rats

| Administration route | i.v. administration | p.o. administration |
|---|---|---|
| dosage | 2 mg/kg | 10 mg/kg |
| Concentration of administered formulation | 1.5 mg/ml | 0.75 mg/ml |
| Dosing volume | 2 ml/kg | 4 ml/kg |
| Dosing vehicle | DMSO/Tween 20/deionized water(1/0.5/28.5) | |
| Testing animals | 3 SD rats per group | |
| Blood-collection time point | 0.08, 0.25, 0.5, 1, 2, 4, 8, 24 hours | |

6. LC-MS/MS (UPLC-MS/MS: liquid chromatography Waters Acquity UPLC (USA) and mass spectrometry 5500 Q Trap (Applied Biosystem/MDS SCIEX) or HPLC-MS\MS (liquid chromatography Agilent 1200 series (USA) and mass spectrometry API 4000 (Applied Biosystem/MDS SCIEX)) was used to determine the concentration of the compound in the plasma. Typical detection conditions are as follows:

| | |
|---|---|
| HPLC | Agilent 1200 Series |
| Mobile phase gradient | A) acetonitrile (0.1% FA); B) water (0.1% FA) 0-2.5 min, A:B 22:75-95:5 2.5-5.0 min, A:B 95:5 5.0-8 min, A:B 22:75 |
| column | XSELECT C18 (2.1*50 mm, 3.5 um) |
| Column temperature | 45° C. |
| Flow rate | 0.6 ml/min |
| Injected dose | 5 ul |

| | |
|---|---|
| UPLC | Waters™ Acquity UPLC |
| Mobile phase gradient | A) methanol (0.1% FA); B) water (0.1% FA) 0-1.5 min, A:B 10:90-95:5 1.5-3.0 min, A:B 95:5 3.0-4.5 min, A:B 10:90 |
| column | Acquity C18 (2.1*50 mm, 2.5 um) |
| Column temperature | 45° C. |
| Flow rate | 0.6 ml/min |
| Injected dose | 1 ul |

The pharmacokinetic parameters were calculated using the pharmacokinetic professional software WinNonlin [Model: Phoenix™ WinNonlin® 6.1; Manufacturer: Pharsight Corporation]. [Phoenix 1.1 User's Guide: p 251-p 300]

According to the above experimental method, the compound (R)-5-amino-3-(4-((5-chloropyridin-2-yl) oxy)phenyl)-1-(4-cyano-4-azaspiro[2.5]oct-6-yl)-1H-pyrazole-4-carboxamide (I) exhibits good bioavailability (>40%).

EXAMPLE 13 hERG Binding Assay (Dofetillide Method)

The IC50 value of a compound for hERG inhibition can be determined according to the method described in the patent application US20050214870 A1. Compound (R)-5-amino-3-(4-((5-chloropyridin-2-yl)oxy)phenyl)-1-(4-cyano-4-azaspiro[2.5]oct-6-yl)-1H-pyrazole-4-carboxamide (I) has very low or no inhibitory effect on hERG, with an IC50 value greater than 1000 nM.

EXAMPLE 14

Pharmacodynamic Assay

Severe immunodeficiency NOD.SCID mice were purchased from Beijing Vital River Laboratory Animal Technology Co., Ltd., and were housed in SPF grade animal room. After TMD-8 cells were cultured to the sufficient amount, the cells were collected by centrifugation and washed twice with PBS. Finally, the cells were resuspended in serum-free RPMI 1640 medium and Matrigel (1:1 v/v). 0.2 ml of cell suspension was injected subcutaneously on the right flank of each mouse using 1 ml syringe and 25G syringe needle. The tumor size was measured with a caliper after about one week post injection. The tumor volume was calculated according to the following formula: tumor volume=(length×width$^2$)/2. When the tumor volume reached about 100-200 mm$^3$, the mice were grouped and p.o. administered daily for 21 days.

Figure 2:
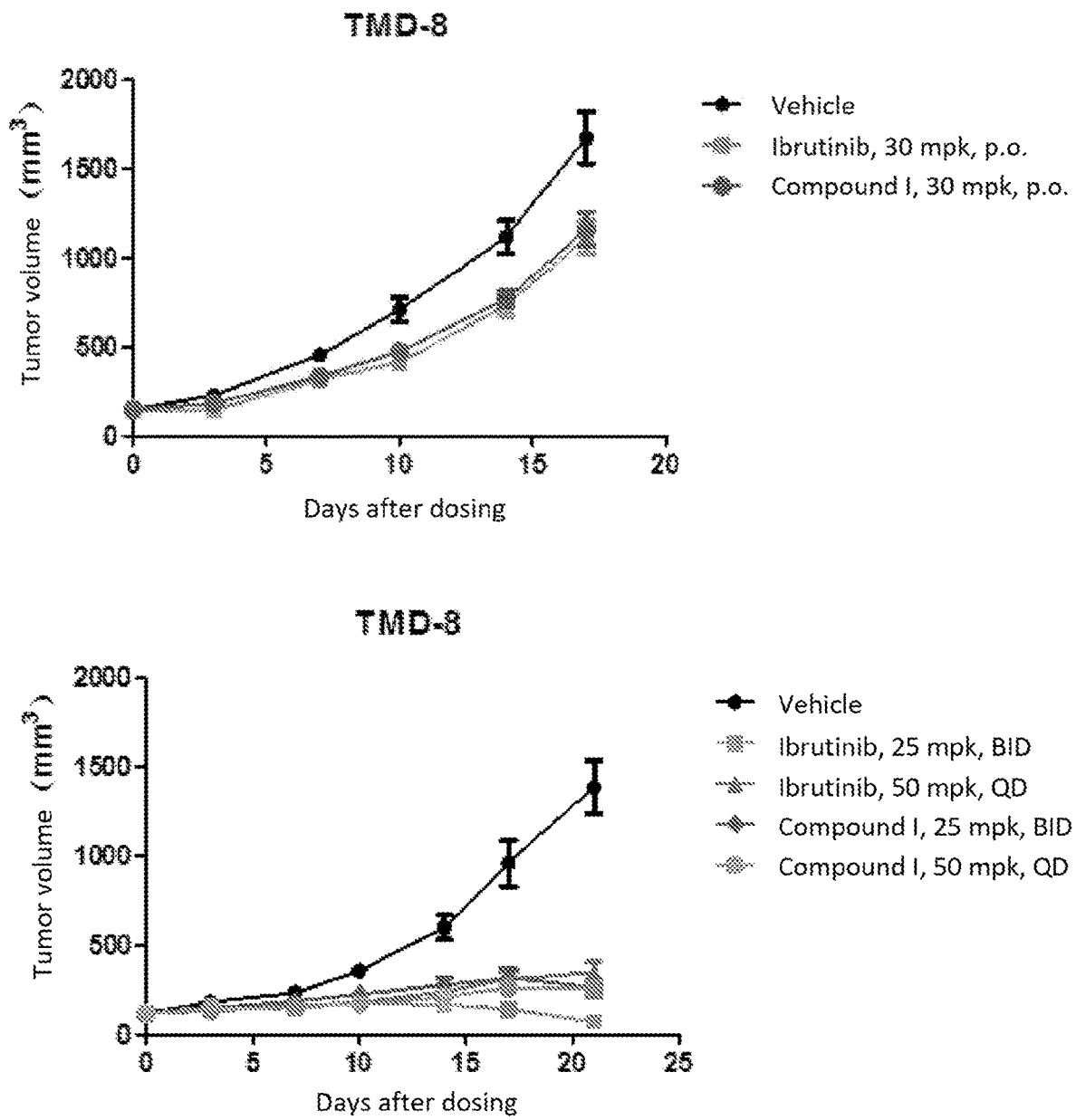
FIG. 2 shows graphs illustrating that the compound of the present invention significantly inhibited the growth of TMD-8, a diffuse large B-cell lymphoma cell line, in vivo, and showed the same anti-tumor effect as the control compound, Ibrutinib.

Compound (R)-5-amino-3-(4-((5-chloropyridin-2-yl)oxy)phenyl)-1-(4-cyano-4-azaspiro[2.5]oct-6-yl)-1H-pyrazole-4-carboxamide (I) significantly inhibited the growth of diffuse large B-cell lymphoma cell line TMD-8 in vivo and showed the same anti-tumor effects as the control compound Ibrutinib (see FIG. 2 for experimental results).

What is claimed is:

1. A crystalline form I of a 5-aminopyrazole carboxamide compound as shown in Formula (I):

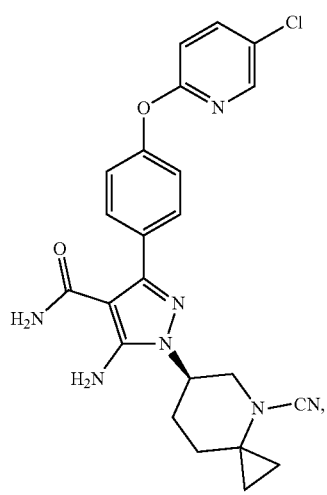

(I)

characterized in that the crystalline form has X-ray powder diffraction characteristic peaks (±0.2°) at 5.8, 9.3, 10.9, 16.4, 18.4, 20.3, 20.9, 21.8, 22.4, 23.0, 24.4, 27.1, 30.0, 31.2, and 31.9.

2. The crystalline form I of claim 1, characterized in that the crystalline form I has an X-ray powder diffraction pattern as shown in FIGS. 1.

3. A method for preparing the crystalline form I of the 5-aminopyrazole carboxamide compound as shown in Formula (I) of claim 1, comprising the steps of:

dissolving the 5-aminopyrazole carboxamide compound as shown in Formula (I) in a good solvent;

then adding a poor solvent to the resulting solution while stirring to give a suspension;

centrifuging the suspension after continued stirring; and drying the resulting solid under vacuum to afford the crystalline form I of the 5-aminopyrazole carboxamide compound as shown in Formula (I);

wherein the good solvent is selected from tetrahydrofuran, and the poor solvent is selected from the group consisting of water and n-heptane; and wherein the ratio of the good solvent to the poor solvent ranges from 1:2 (v/v) to 1:4 (v/v).

4. The method of claim 3, wherein the good solvent is tetrahydrofuran, and the poor solvent is water or n-heptane; and wherein the ratio of the good solvent to the poor solvent is 1:2 (v/v).

5. The method of claim 3, wherein the good solvent is tetrahydrofuran, and the poor solvent is n-heptane; and wherein the ratio of the good solvent to the poor solvent is 1:4 (v/v).

6. A pharmaceutical composition comprising the crystalline form I of the 5-aminopyrazole carboxamide compound as shown in Formula (I) of claim 1 and a pharmaceutically acceptable carrier.

7. A method of treating a disease mediated by BTK, which is selected from the group consisting of a xenoimmune condition or disease, a thromboembolic disease, and diffuse large B-cell lymphoma, comprising administering the crystalline form I of the 5-aminopyrazole carboxamide compound of claim 1.

* * * * *